US012624402B2

(12) United States Patent
Okino

(10) Patent No.: US 12,624,402 B2
(45) Date of Patent: May 12, 2026

(54) VARIANT CLASSIFICATION THROUGH HIGH-CONFIDENCE MUTATION DETECTION FROM FLUORESCENCE SIGNALS MEASURED WITH A MULTIPLE MUTATION ASSAY

(71) Applicant: Bio-Rad Laboratories, Inc., Hercules, CA (US)

(72) Inventor: Steven Okino, Pleasant Hill, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 462 days.

(21) Appl. No.: 18/234,573

(22) Filed: Aug. 16, 2023

(65) Prior Publication Data

US 2024/0076751 A1 Mar. 7, 2024

Related U.S. Application Data

(60) Provisional application No. 63/403,581, filed on Sep. 2, 2022.

(51) Int. Cl.
| | |
|---|---|
| *C12Q 1/70* | (2006.01) |
| *C12Q 1/6827* | (2018.01) |
| *C12Q 1/6844* | (2018.01) |
| *C12Q 1/6851* | (2018.01) |
| *G01N 33/58* | (2006.01) |

(52) U.S. Cl.
CPC ............. *C12Q 1/70* (2013.01); *G01N 33/582* (2013.01); *G01N 2800/26* (2013.01)

(58) Field of Classification Search
CPC ........ C12Q 1/70; C12Q 1/701; C12Q 1/6851; G01N 2800/26; G01N 33/582
See application file for complete search history.

(56) References Cited

U.S. PATENT DOCUMENTS

2010/0250145 A1 9/2010 Houser

FOREIGN PATENT DOCUMENTS

| WO | WO 2021/213163 A1 | 10/2021 |
| WO | WO 2022/018685 A1 | 1/2022 |

OTHER PUBLICATIONS

PCT International Search Report and Written Opinion, PCT Application No. PCT/US2023/030341, Nov. 29, 2023, 13 pages.
Rowan, A. G. et al., "Optimized protocol for a quantitative SARS-CoV-2 duplex RT-qPCR assay with internal human sample sufficiency control," Journal of Virological Methods, Epub. May 10, 2021, vol. 294, article No. 114174, pp. 1-7.
Toptan, T. et al., "Optimized qRT-PCR Approach for the Detection of Intra- and Extra-Cellular SARSCoV-2 RNAs," Int. J. Mol. Sci., Jun. 20, 2020, vol. 21, article No. 4396, pp. 1-11.

*Primary Examiner* — Barry A Chestnut
(74) *Attorney, Agent, or Firm* — Fenwick & West LLP

(57) ABSTRACT

A system and method for SARS-CoV-2 variant classification through mutation detection from qPCR fluorescence signals. The system receives fluorescence signals, wherein a first fluorescence signal indicates quantitative presence of a first genomic region as a control for SARS-CoV-2, and a second fluorescence signal indicates quantitative presence of a second genomic region of a first mutation present in a subset of variants of SARS-CoV-2. The system measures a first Cq for the first fluorescence signal and a second Cq for the second fluorescence signal as the signals cross a threshold RFU. The system calculates a delta Cq as a difference between the two. Further, the system identifies a first peak RFU for the first fluorescence signal and a second peak RFU for the second fluorescence signal, and calculates a RFU ratio of the two. The system detects presence of the first mutation based on the delta Cq and/or the RFU ratio.

20 Claims, 7 Drawing Sheets

110

120

125

130

105

Fluorescence
Signal

100

Analytics System
100

| Signal Processor 140 | Detection Model 150 | Notification Generator 160 |

Sample Database 145

Variant Database 155

200

Sample Collection
210

Perform qPCR
220

Pre-Analysis Processing
230

Analyses
240

Detect presence of
mutations
242

Search for
known variant
244

Return Notification
250

Multiple Mutation Assay
300

310       320       330       340       350

400

VARIANT CLASSIFICATION THROUGH HIGH-CONFIDENCE MUTATION DETECTION FROM FLUORESCENCE SIGNALS MEASURED WITH A MULTIPLE MUTATION ASSAY

CROSS-REFERENCE TO RELATED APPLICATIONS

This applications claims the benefit of and priority to U.S. Provisional Application No. 63/403,581 filed on Sep. 2, 2022, which is incorporated by reference in its entirety.

BACKGROUND

Field of the Art

This present disclosure generally relates to classification of virus variants from nucleic acid samples.

Traditional systems detect presence of a polynucleotide sequence in a quantitative Polymerase Chain Reaction (qPCR) operation by measuring whether there is sufficiently high fluorescence signal, e.g., above an agnostic baseline level of noise. These traditional systems, however, are prone to high levels of detecting false positives as true positives. Utilizing the simple noise baseline is inadequately positioned to provide accurate high-confidence detection.

SUMMARY

A system is disclosed for identifying infections (e.g., viral or bacterial) based on analysis of quantitative fluorescence signal targeting polynucleotide sequences. In some embodiments, the system is implemented for SARS-CoV-2 variant classification. The system may include a thermal cycler and an analytics system. The thermal cycler is configured to cycle through various temperature points for varying durations. For example, in a polymerase-based amplification reaction (e.g., quantitative Polymerase Chain Reaction (qPCR)), the thermal cycle can cycle through a denaturation phase, an annealing phase, and an extension phase to amplify target genomic regions. The target probes used in the qPCR operation may include primers with fluorophores bound to the primers. The thermal cycler includes one or more light sources for exciting the fluorophores on the extended amplificons and one or more light detectors for measuring fluorescence signal from a sample. The system may use a multiple mutation assay that includes a control probe targeting a genomic region common to the virus or the bacterium and probes targeting particular mutations of variants of the virus or the bacterium. In embodiments screening for SARS-CoV-2 variants, the multiple mutation assay includes the control probe common to all SARS-CoV-2 variants and one or more mutation probes targeting genomic regions encompassing various mutations present in SARS-CoV-2 variants. The multiple mutation assay may distinctly target mutations, such that each variant has a distinct set of target mutations from other variants.

The analytics system analyses the fluorescence signals to determine whether the sample has one of the variants. The analytics system measures a quantitative cycle (Cq) for each fluorescence signal that crosses a threshold relative fluorescence unit (RFU). The analytic system may calculate a delta Cq for each mutation fluorescence signal by taking a difference between the Cq of the mutation fluorescence signal and the Cq of the control fluorescence signal. The analytics system may measure a peak RFU for each fluorescence signal. The peak RFU may be a maximum RFU over the duration of the fluorescence signal, or at a sample thermal cycle (e.g., the final thermal cycle). The analytics system may calculate a RFU ratio for each mutation fluorescence signal as a ratio of the peak RFU for the mutation fluorescence signal to the peak RFU for the control fluorescence signal. The analytics system may, with high-confidence, detect presence of a target polynucleotide sequence (e.g., a mutation) by comparing a strength of the fluorescence signal for the target polynucleotide sequence to a strength of the fluorescence signal for the control sequence. The comparative strengths of the fluorescence signals may be based on the delta Cq being below a Cq tolerance and/or the RFU ratio being above a RFU tolerance. The analytics system may further determine a mutation pattern for the sample based on the detected presence or absence of the mutations screened for in the multiple mutation assay. The analytics system searches for known variants matching the mutation pattern of the sample.

In response to the analytics, the analytics system may perform actions based on the results. The analytics system may generate and report a notification based on the results. If a known variant is matched, having the same set of mutations (also referred to as "mutation pattern") as the test sample, then the analytics system may report the known variant. The analytics system may further provide a treatment recommendation based on the identified known variant. The analytics system may also report variant metrics calculated based on classified samples. For example, the analytics system may provide aggregated statistics on how many samples are being classified as each variant. These statistics can inform researchers on variant behavior. In embodiments with no identified variant, the analytics system may report the closest match. The analytics system may also notify that there may be a candidate new variant for sequencing. The analytics system may transmit such notifications to a client computing device for a laboratory clinician, a researcher, a healthcare provider, a patient, another health-care-related professional, or some combination thereof.

Figure 1A:
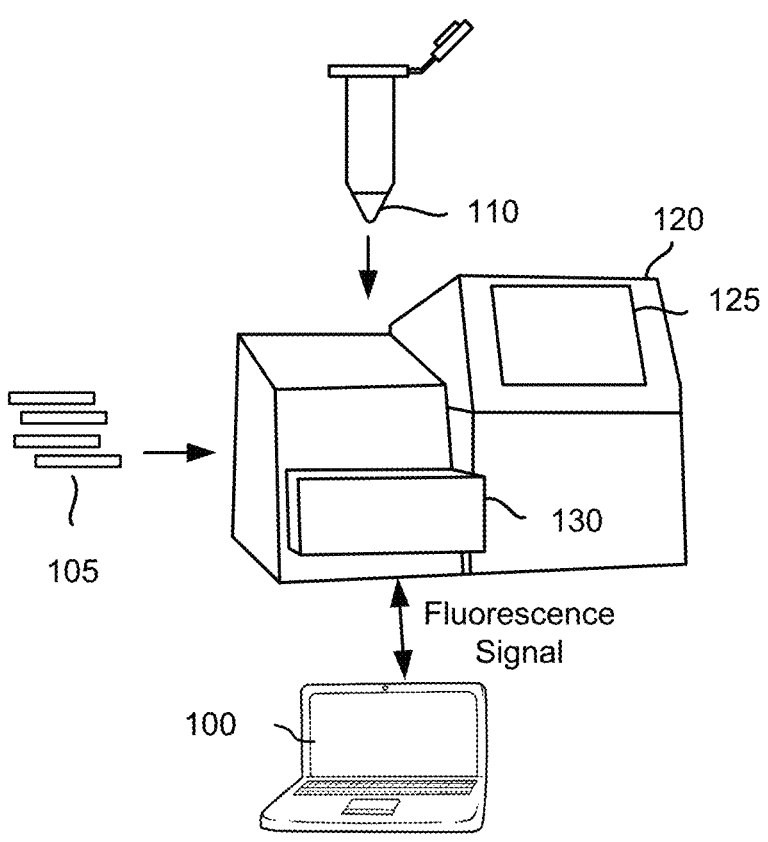
FIG. 1A illustrates an exemplary flowchart of devices for quantifying nucleic acid presence in a thermal cycler, according to one or more embodiments.

The figures and the following description describe certain embodiments by way of illustration only. One skilled in the art will readily recognize from the following description that alternative embodiments of the structures and methods may be employed without departing from the principles described. Wherever practicable, similar or like reference numbers are used in the figures to indicate similar or like functionality. Where elements share a common numeral followed by a different letter, this indicates the elements are similar or identical. A reference to the numeral alone generally refers to any one or any combination of such elements, unless the context indicates otherwise.

DETAILED DESCRIPTION

Overview

A system for SARS-CoV-2 variant classification performs high-confidence mutation detection from fluorescence signals. The system uses a multiple mutation assay that includes a control probe targeting a genomic region on the SARS-CoV-2 virus and one or more mutation probes targeting genomic regions encompassing various mutations present in SARS-CoV-2 variants. The multiple mutation assay may distinctly target mutations, such that each variant has a distinct set of target mutations. The multiple mutation assay is used in a thermal cycler to amplify and quantify signal of the mutations and the control.

The analytics system analyses the fluorescence signals to classify the sample as having a variant. The analytics system may measure a quantitative cycle (Cq) for each fluorescence signal that crosses a threshold relative fluorescence unit (RFU). The analytic system may calculate a delta Cq for each mutation fluorescence signal by taking a difference between the Cq of the mutation fluorescence signal and the Cq of the control fluorescence signal. The analytics system may measure a peak RFU for each fluorescence signal. The peak RFU may be a maximum RFU over the duration of the fluorescence signal, or at a sample thermal cycle (e.g., the final thermal cycle). The analytics system may calculate a RFU ratio for each mutation fluorescence signal as a ratio of the peak RFU for the mutation fluorescence signal to the peak RFU for the control fluorescence signal. The analytics system may, with high-confidence, detect presence of a mutation based on the delta Cq being below a Cq tolerance and/or the RFU ratio being above a RFU tolerance. The analytics system may further determine a mutation pattern for the sample based on the detected presence or absence of the mutations screened for in the multiple mutation assay. The analytics system searches for known variants matching the mutation pattern of the sample.

The analytics system generates and reports a notification based on the results. If a known variant is matched, having the same set of mutations (also referred to as "mutation pattern") as the test sample, then the analytics system may report the known variant. The analytics system may further provide a treatment recommendation based on the identified known variant. The analytics system may also report variant metrics calculated based on classified samples. For example, the analytics system may provide aggregated statistics on how many samples are being classified as each variant. These statistics can inform researchers on variant behavior. In embodiments with no identified variant, the analytics system may report the closest match. The analytics system may also notify that there may be a candidate new variant for sequencing. The analytics system may transmit such notifications to a client computing device for a laboratory clinician, a researcher, a healthcare provider, a patient, another healthcare-related professional, or some combination thereof.

FIG. 1A is an exemplary flowchart of devices for quantifying nucleic acid presence in a thermal cycler 120, according to one or more embodiments. This illustrative flowchart includes devices such as a thermal cycler 120 and an analytics system 100. The thermal cycler 120 and the analytics system 100 may work in tandem to perform one or more steps in the processes. Generally, the thermal cycler 120 and the analytics system 100 may be used to identify variants of a virus or other microbe. Although the following description is centered around variant classification of the SARS-CoV-2 virus, the methodologies generally described can be applied to any other virus or microbe.

In various embodiments, the thermal cycler 120 receives a nucleic acid sample 110. As shown in FIG. 1A, the thermal cycler 120 can include a graphical user interface 125 that enables user interactions with particular tasks (e.g., initiate thermal cycling or terminate thermal cycling) as well as one more loading stations 130 for loading the samples. The thermal cycler 120 may also load necessary primers 105 and/or buffers for performing the quantification assays. The primers 105 may be for targeted probes to detect particular genetic sequences. Each targeted probe for quantitative amplification may include a pair of primers, a forward primer and a reverse primer placed on either end of the targeted genetic sequence. Each primer is a single-stranded polynucleotide of short length, e.g., less than 30, 25, 20, 15, or 10 nucleotides. Each primer may further have a fluorophore or fluorescent dye bound to the primer. The fluorophore or fluorescent dye is a chemical compound that can re-emit light when light excites the fluorophore.

Once a user of the thermal cycler 120 has provided the necessary reagents and cartridge to the loading station 130 of the thermal cycler 120, the user can initiate thermal cycling by interacting with the graphical user interface 125 of the thermal cycler 120. The thermal cycler 120 may also be configured for sample multiplexing, i.e., performing separate thermal cycling algorithms for each of a plurality of samples. Once initiated, the thermal cycler 120 performs the thermal cycling and outputs fluorescence signals from each nucleic acid sample 110 to the analytics system 100.

In some embodiments, the thermal cycler 120 is communicatively coupled with the analytics system 100. The analytics system 100 includes some number of computing devices used for processing the data transmitted from the thermal cycler 120, for various applications such as assessing virus variant classification, false positive detection, or quality control. The analytics system 100 can be communicatively coupled to the thermal cycler 120 through a wireless, wired, or a combination of wireless and wired communication technologies. Generally, the analytics system 100 is configured with a processor and non-transitory computer-readable storage medium storing computer instructions that, when executed by the processor, cause the processor to process the data output by the thermal cycler 120 or to perform one or more steps of any of the methods or processes disclosed herein.

Figure 1B:
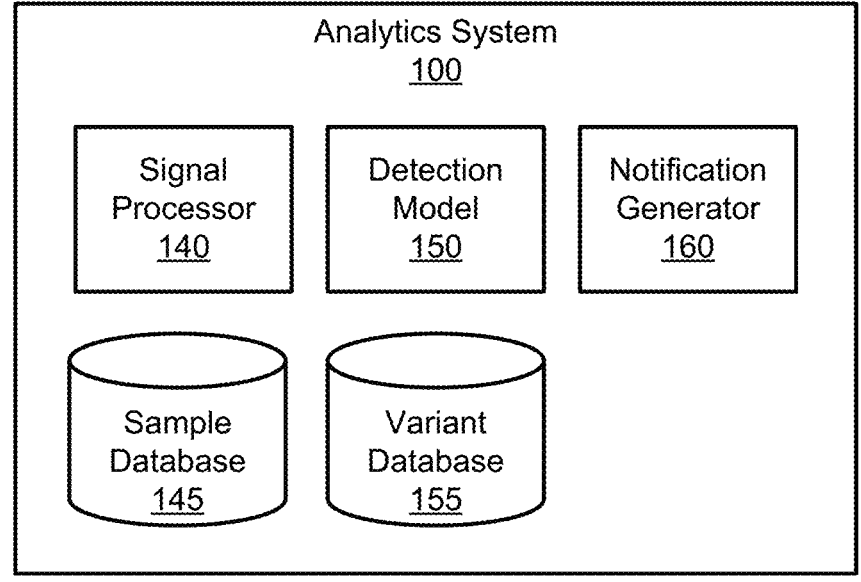
FIG. 1B is a block diagram of an analytics system for processing data from the thermal cycler, according to one or more embodiments.

FIG. 1B is a block diagram of an analytics system 100 for processing nucleic acid samples according to one embodiment. The analytics system 100 implements one or more computing devices for use in analyzing the samples. The analytics system 100 includes a signal processor 140, a sample database 145, a detection model 150, a variant database 155, and a notification generator 160. In some embodiments, the analytics system 100 performs some or all of the processes described throughout this disclosure.

The signal processor 140 processes data received from the thermal cycler 120, including, but not limited to, fluorescence signals resulting from quantitative amplification. The signal processor 140 may process the fluorescence signal, e.g., filtering out noise, normalizing the signals, detecting thermal cycling errors, or other pre-analysis processing steps, etc. The signal processor 140 may also label fluorescence signals based on the fluorescence wavelength. For example, one probe may fluoresce at a first wavelength of light, where as another probe may fluoresce at a second wavelength of light that is different than the first wavelength of light. The signal processor 140 may identify a fluorescence signal close to the first wavelength of light (e.g., within some tolerance) as indicative of quantification of the first probe and a fluorescence signal close to the second wavelength of light (e.g., within some tolerance) as indicative of quantification of the second probe. The signal processor 140 may further collate the fluorescence signals for each of the various samples.

The sample database 145 stores the samples including the fluorescence signals measured by the thermal cycler 120. The sample database 145 may include information identifying an individual of each of the samples. Each sample may also be stored with metadata, e.g., indicating a timestamp, a thermal cycling algorithm, how many other samples were run on the same cartridge, etc.

The detection model 150 detects presence or absence of the genomic regions targeted by the one or more probes. The signal processor 140 may detect presence of the targeted genomic regions by comparing the fluorescence signals to a control fluorescence signal for a control probe. In one or more embodiments, the signal processor 140 positively identifies presence of a targeted genomic region in the nucleic acid sample based on satisfaction of one or more detection criteria. One detection criterium is whether a fluorescence signal for a mutation probe is within a delta quantitative cycle (Cq) tolerance from a control fluorescence signal. Another detection criterium is whether a relative fluorescence unit (RFU) ratio of a fluorescence signal for a mutation probe to the control fluorescence signal is above a RFU tolerance. Additional details relating to detecting presence of a mutation is further described in FIGS. 2-5.

The detection model 150 may also classify a sample as having a particular SARS-CoV-2 variant. The detection model 150 utilizes the fluorescence signals measured with the multiple mutation assay to detect presence of mutations. Each known variant is generally sequenced with a known set of mutations (also referred to as a "mutation pattern"). Based upon detected mutations, the detection model 150 may classify a sample as having one of the known variants. The multiple mutation assay may be designed to include mutations to distinctly classify between the known variants. For example, the multiple mutation assay may be designed to avoid two or more distinct variants having the same mutation pattern targeted by the multiple mutation assay. In some embodiments, the multiple mutation assay is further designed to include the smallest set of target mutations that is still capable of distinguishing between the known variants.

The variant database 155 stores information on known variants. Known variants are generally variants that have been sequenced to identify the genomic sequence of the variant. The genomic sequence informs what mutations are present in the variant. Samples having the same variant exhibit the same set of mutations or the same mutation pattern. Samples of differing variants exhibit different mutations. The variant database 155 may further store variant metrics on the classified samples, for example, tallying how many samples have been classified for each variant, first discovery of an unknown variant in a sample, other information relating to classified samples, etc. Such metrics may inform researchers and clinicians on variant behavior. For example, there is a sudden spike in samples being classified as one variant, indicating an oncoming wave. In another example, multiple samples are classified as having an unknown variant, indicating a recent evolution causing a new variant.

The notification generator 160 generates notifications reporting analyses by the analytics system 100. The notification generator 160 may generate separate notifications base on the analyses. In some embodiments, the notification generator 160 generates a notification for a classified sample indicating the variant classification. The variant classification may include a known variant that the sample is classified as having, a treatment recommendation for the sample, providing an error in classification, notifying a candidate new variant (e.g., for further sequencing), or some combination thereof. The notification generator 160 may also provide notifications based on the variant metrics. For example, the notification generator 160 may provide a notification of an oncoming wave for a variant when a threshold number of samples have been classified as having the variant. As another example, the notification generator 160 may provide a notification of a candidate new variant upon identification of a threshold number of samples having a set of mutations not attributable to the known variants. The notification generator 160 may transmit the notifications to other client devices, e.g., belonging to a researcher, a clinician, a healthcare provider, a patient, etc.

SARS-CoV-2 Variant Classification

Figure 2:
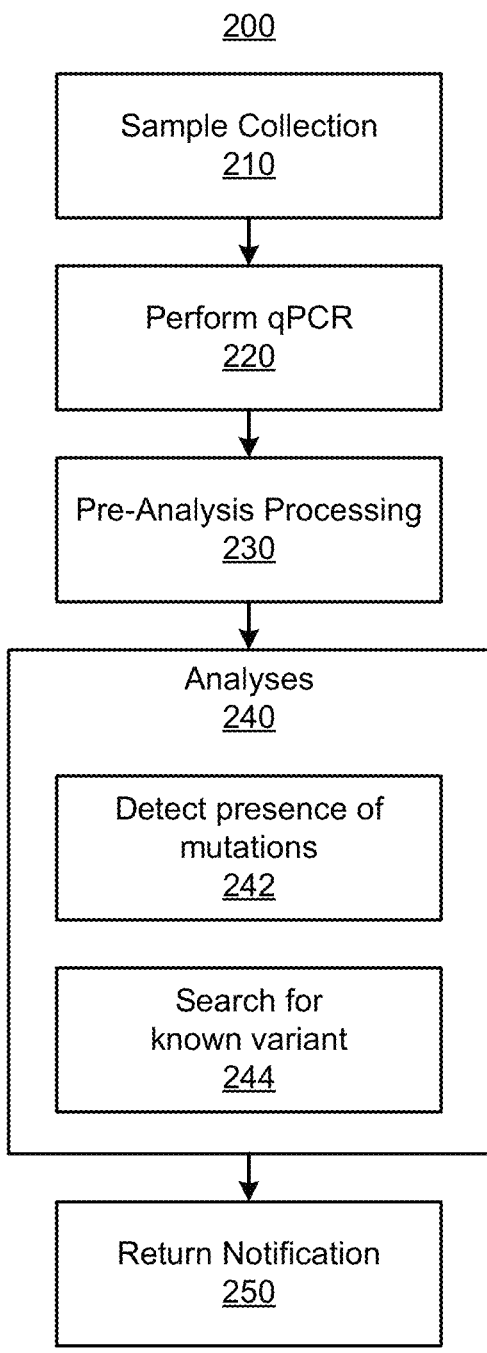
FIG. 2 illustrates a flowchart for classifying a SARS-CoV-2 variant using a multiple mutation assay in a quantitative thermal cycling operation, according to one or more embodiments.

FIG. 2 is a flowchart illustrating a process 200 for classifying a SARS-CoV-2 variant using a multiple mutation assay in a quantitative thermal cycling operation, according to one or more embodiments. The various devices in FIG. 1A may be used to perform one or more steps of the process 200. In other embodiments, the process 200 includes different steps, a different combination of steps, additional steps, fewer steps, or some combination thereof.

In the embodiment shown in FIG. 2, the process 200 begins with a healthcare provider collecting 210 a nucleic acid sample from a patient. The healthcare provider may be a laboratory clinician, a doctor, or another healthcare-related employee. Alternatively, the sample may be self-collected by the patient (or a friend or family member of the patient). The nucleic acid sample collected may be tissue biopsy, blood, whole blood, plasma, serum, urine, cerebrospinal fluid, fecal, saliva, sweat, tears, pleural fluid, pericardial fluid, or peritoneal fluid of the patient. Depending on the type of sample, the healthcare provider may process the nucleic acid sample for performing the quantitative thermal cycling. The sample includes genetic material belonging to the patient, which may be quantified for SARS-CoV-2 variant classification. To prepare for thermal cycling, the healthcare provider or the thermal cycler 120 may mix the nucleic acid sample with probes, reagents, buffers, chemicals, enzymes, catalysts, or some combination thereof. For example, for performing a qPCR operation, the nucleic acid sample may be lysed to expose the nucleic acid, mixed with probes, nucleoside triphosphates (NTPs) or deoxynucleoside triphosphates (dNTPs), and a polymerase. The multiple mutation assay includes a control probe and multiple mutation probes. The control probe targets a control genetic sequence present in all SARS-CoV-2 viruses. The mutation probes target genetic sequences specific to mutations present in various SARS-CoV-2 variants. Each probe may include two primers, a forward primer and a reverse primer, located on opposite ends of the targeted genetic sequence. In some embodiments, the thermal cycler 120 may mix the needed components with an input nucleic acid sample. Along with the sample, the healthcare provider may collect other information relating to the individual, e.g., biological sex, age, ethnicity, smoking status, any prior diagnoses, etc.

The thermal cycler 120 perform 220 the qPCR on the sample. The thermal cycler 120 performs the qPCR according to an algorithm. The algorithm may dictate temperatures to adjust the sample to and periods for each temperature. The algorithm may further dictate a number of cycles for the qPCR, e.g., 15, 20, 25, 30, 35, 40, 45, 50, 55, or 60 cycles. Generally, a qPCR includes a denaturation phase, an annealing phase, and an extension phase. The qPCR operation continues to cycle through the three phases. In the denaturation phase, the temperature is set at a high point (e.g., 95° C.) which denatures the nucleic acid, e.g., splitting DNA apart into the complementary strands or unfolding RNA. In the annealing phase, the temperature is set at a lower point (e.g., between 50° C. and 60° C.) where primers are annealed to the denatured strands. In the extension phase, the temperature is set at a medium point (e.g., between 68° C. and 72° C.) which allows for the polymerase to bind to the primers and to tack on nucleotides (e.g., NTPs or dNTPs) extending the nucleic acid fragments from the annealed primers. In a RT-qPCR operation, one or more fluorophores (also referred to as fluorescent dyes) are bound to the primers. As the qPCR operation amplifies the targeted genomic regions, the fluorophores are excited to emit light that is detected to generate the fluorescence signals. The thermal cycler 120 is configured with one or more light sources for exciting the fluorescent dyes and one or more light detectors to measure an amount of light detected (e.g., measured in RFU). The thermal cycler 120 measures the fluorescence signals for each sample over the course of the qPCR operation. The thermal cycler 120 provides the fluorescence signals to the analytics system 100.

The thermal cycler 120 may also multiplex qPCR operations across multiple samples on one cartridge. One thermal cycler 120 block may include wells to receive multiple samples (e.g., 96-well block). Each well may receive one sample, e.g., totaling the ability to perform qPCR on 96 samples. The thermal cycler 120 may further include individualized light source(s) and/or light detector(s) for each well.

The analytics system 100 receives the fluorescence signals from the thermal cycler 120 and performs pre-analysis processing 230. Pre-analysis processing 230 may include labeling the fluorescence signals for a sample based on the known probes used in the multiple mutation assay. The analytics system 100 may obtain information on the probes used in the multiple mutation assay. Each probe is designed to target a genetic sequence specific to a particular mutation. In some embodiments, of the fluorescence signals measured for a sample, at least one fluorescence signal is a control fluorescence signal for a control genetic sequence present in all SARS-CoV-2 viruses. The fluorescence signals may further include mutation fluorescence signals corresponding to the mutation genetic sequences. Each probe (control or mutation) has a fluorophore that emits at a specific wavelength of light, distinct from the other probes to avoid any merging or mismatching of fluorescence signals. The analytics system 100 can identify which fluorescence signal belongs to which probe based on the signal wavelengths. For example, a control probe has a fluorophore that emits yellow visible light (with wavelength ~590 nm). The analytics system 100 identifies the fluorescence signal with the wavelength ~590 nm as relating to the control probe. The analytics system 100 may likewise identify the remaining fluorescence signals as relating to the other probes used in the multiple mutation assay. The analytic system 100 may perform other pre-analysis processes to prepare the fluorescence signals for the downstream analyses, including SARS-CoV-2 variant classification.

The analytics system 100 performs analyses 240 to classify a SARS-CoV-2 variant for the sample. The analyses 240 may include detecting 242 presence of mutations and searching 244 for known variants. The analytics system 100 detects 242 the presence of mutations by comparing the mutation fluorescence signals to the control fluorescence signal. Based on certain detection criteria, the analytics system 100 detects the presence of the mutations to a high degree of confidence. Detecting 242 presence of the mutations is further described in FIG. 4. The analytics system 100 searches 244 for a known variant by comparing the detected mutations for a sample to combination of mutations for the known variants. If the combination of detection mutations for the sample does not align with any combination of mutations for the known variants, then the analytics system 100 may determine the sample to be a candidate new variant. If the combination of mutations for the sample aligns with a combination of a known variant, then the analytics system 100 may return a prediction that the sample is that matched known variant. Searching 244 for a known variant is further described in FIG. 4.

The analytics system 100 may return 250 the notification detailing results of the analyses 240. For example, the notification may indicate a variant prediction between a known variant or a candidate new variant. The notification may also indicate a treatment recommendation in addition to the variant prediction. In other instances, the notification may indicate an error in the sample (e.g., whether in sample collection, running the qPCR, etc.). Notifications may further suggest follow-up steps. For example, an error notification may suggest collecting a new sample, or performing another qPCR operation. In another example, a notification of a candidate new variant may include a recommendation to sequence the candidate new variant, e.g., for submission to the World Health Organization and/or Center for Disease Control.

Figure 3:
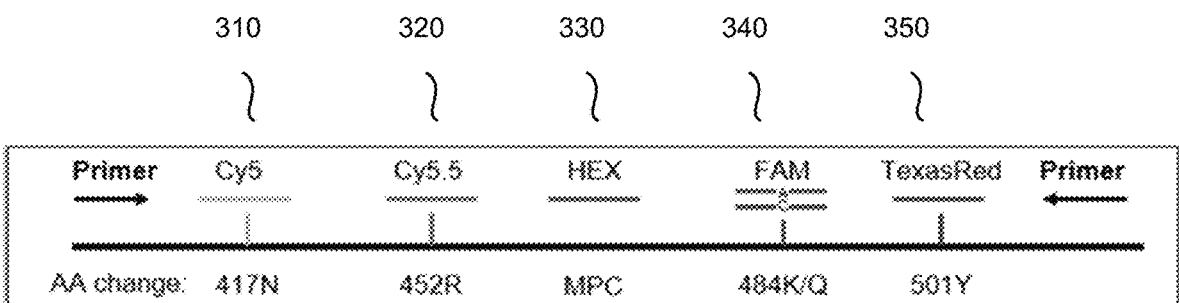
FIG. 3 illustrates a multiple mutation assay, according to one or more embodiments.

FIG. 3 illustrates an example multiple mutation assay 300, according to one or more embodiments. The multiple mutation assay 300 includes five probes targeting different genomic regions in the SARS-CoV-2 virus's genetic material. The five probes include a control probe 330 with a HEX fluorophore. There are four other mutation probes targeting various mutations in the SARS-CoV-2 genome, including: a first mutation probe 310 targeting a 471N mutation with a Cy5 fluorophore, a second mutation probe 320 targeting a 452R mutation with a Cy5.5 fluorophore, a third mutation probe 340 targeting a 484K/Q mutation with a FAM fluorophore, and a fourth mutation probe 350 targeting a 501Y mutation with a TexasRed fluorophore. Additional multiple mutation assays that may be used are further described in Appendix A entitled "Detection of Gene Variants," which is a part of this disclosure and specification. Note that Appendix A describes specific embodiments and that any statement or implication that certain features or elements are required are only required for those embodiments and may not be present in other embodiments.

Figure 4:
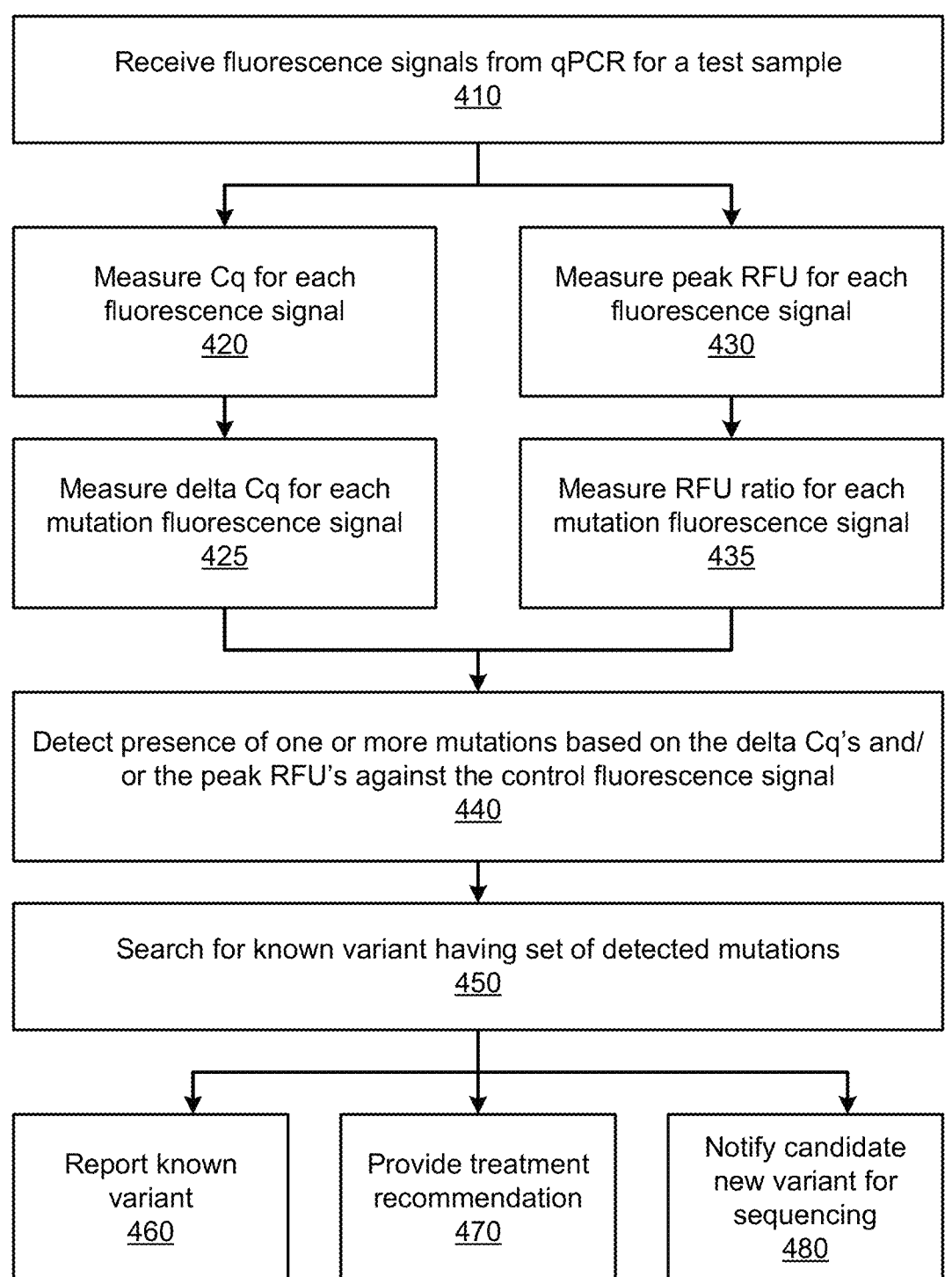
FIG. 4 illustrates a flowchart for classifying a SARS-CoV-2 variant based on fluorescence signals measured by the thermal cycling operation, according to one or more embodiments.

FIG. 4 is a flowchart of a classifying process 400 a SARS-CoV-2 variant based on fluorescence signals, according to one or more embodiments. The classifying process 400 the SARS-CoV-2 variant is an embodiment of the analyses 240 in FIG. 2. The description of FIG. 4 is in the perspective of the analytics system 100 performing the various steps; however, in other embodiments, other devices shown in FIG. 1A may perform some of the steps. In other embodiments, there may be different steps, additional steps, fewer steps, a different combination of the steps, or some combination thereof. Further details relating to the SARS-CoV-2 variant classification methodology are provided in Appendix B entitled "Multiple Mutation Assay Instructions for Use," which is a part of this disclosure and specification. Note that Appendix B describes specific embodiments and that any statement or implication that certain features or elements are required are only required for those embodiments and may not be present in other embodiments.

The analytics system 100 receives 410 fluorescence signals from the qPCR for a test sample. The fluorescence signals may include a control fluorescence signal relating to a control probe and a plurality of mutation fluorescence signals relating to mutation probes. Each fluorescence signal charts fluorescence (RFU) at a specific wavelength over the quantitative cycles (Cq) of the qPCR operation. The analytics system 100 may tag each fluorescence signal as corresponding to each probe by comparing the wavelength of the fluorescence signal to the anticipated emission wavelengths of the probes.

The analytics system 100 may measure 420 the Cq that each fluorescence signal crosses a threshold RFU. The threshold RFU may be set from the range of 1 RFU to 500 RFU. The analytics system 100 may set the threshold RFU based on the control fluorescence signal. In one or more embodiments, the analytics system 100 may use baseline subtraction curve fit to identify the threshold RFU that disregards noise RFU. The analytics system 100 may set a threshold RFU for each sample independently. In some embodiments, the analytics system 100 may return an error if there was minimal control fluorescence signal. For example, if the control fluorescence signal is below 500, 450, 400, 350, 300, 250, 200, 150, 100, 50, 40, 30, 20, or 10 RFU, then the analytics system 100 may return an error that may include a recommendation to collect a new sample.

The analytics system 100 may measure a delta Cq for each mutation fluorescence signal against the control fluorescence signal. The analytics system 100 calculates a delta Cq for a first mutation fluorescence signal by taking a difference between the Cq for the first fluorescence signal that crosses the threshold RFU and the Cq for the control fluorescence signal that crosses the threshold RFU. The analytics system 100 may calculate similarly for each of the mutation fluorescence signals. The delta Cq may be an absolute difference or may include a sign (positive or negative) indicating whether the mutation fluorescence signal's Cq is smaller or greater than the control fluorescence signal's Cq.

The analytics system 100 may measure 430 a peak RFU for each fluorescence signal. In some embodiments, the peak RFU may be measured as a maximum RFU over the PCR operation. In other embodiments, the peak RFU may be measured at a sample thermal cycle over the PCR operation, e.g., 15, 20, 25, 30, 35, 40, 45, 50 Cq. The sample thermal cycle may also be the final thermal cycle in the PCR operation.

The analytics system 100 may measure 435 a RFU ratio for each mutation fluorescence signal. The RFU ratio is a ratio of the peak RFU of a mutation fluorescence signal to the peak RFU of the control fluorescence signal. Other embodiments, of the RFU ratio utilizes the inverse, i.e., the peak RFU of the control fluorescence signal to the peak RFU of the mutation fluorescence signal.

The analytics system 100 detects presence or absence of the one or more mutations based on delta Cq's and/or the RFU ratios. In one or more embodiments, the analytics system 100 considers both the delta Cq and the RFU ratio to positively identify a mutation from the mutation fluorescence signal. The analytics system 100 may positively identify the mutation, if both the delta Cq (absolute difference) is below a Cq tolerance and the RFU ratio is above a RFU tolerance. The analytics system 100 may, alternatively, positively identify the mutation, if either the delta Cq is below the Cq tolerance or the RFU ratio is above the RFU tolerance. In other embodiments, the analytics system 100 considers just the delta Cq. In yet other embodiments, the analytics system 100 considers just the RFU ratio. In embodiments with delta Cq including a sign (positive or negative), the Cq tolerance may be an asymmetric range (e.g., −6.0 to 4.0) such that the analytics system 100 evaluates whether the delta Cq is within the tolerance range. The analytics system 100 evaluates each and every one of the mutations targeted in the multiple mutation assay. As a result, the analytics system 100 determines presence or absence for each mutation. The analytics system 100 may determine a mutation pattern for the test sample as a set of mutations for the test sample, e.g., each mutation targeted in the multiple mutation assay is positive or negative based on the detection.

The analytic system 100 may set the Cq tolerance and/or the RFU tolerance to achieve a certain confidence score in the positive detections. The analytics system 100 may use a set of training samples with known mutation pattern (e.g., as determined via sequencing of the viral genetic material). The analytics system 100 may perform the SARS-CoV-2 variant classification 400 to predict which mutations are present. The analytic system 100 may utilize the training samples to identify the Cq tolerance and/or the RFU tolerance to achieve the confidence goal. When setting the Cq tolerance and/or the RFU tolerance, the analytics system 100 makes a tradeoff between sensitivity and specificity, wherein high specificity minimizes false positive detections against the known mutation pattern of the training samples. In some embodiments, the Cq tolerance is a Cq value selected from the range of 1 Cq to 10 Cq. In some embodiments, the Cq tolerance is further selected from the range of 2 Cq to 5 Cq. In some embodiments, the RFU tolerance is a ratio selected from the range of 0.3 to 1.1, e.g., 0.30, 0.35, 0.40, 0.45, 0.50, 0.55, 0.60, 0.65, 0.70, 0.75, 0.80, 0.85, 0.90. 0.95, 1.00, 1.05, or 1.10. In some embodiments, wherein the RFU tolerance is further selected from the range of 0.9 to 1.0.

The analytics system 100 searches 450 for a known variant having set of detected mutations. The analytics system 100 may retrieve the known variants, each with distinct mutation pattern. The analytics system 100 searches for whether the mutation pattern of the test sample matches to any mutation pattern for the known variants. If no known variant has a mutation pattern matching to the test sample, then the analytics system 100 may identify a closest match, e.g., whichever mutation pattern has the smallest vector distance or degree of difference from the test sample's mutation pattern.

The analytics system 100 generates a notification based on the results. If a known variant is matched, having the same mutation pattern as the test sample, then the analytics system 100 may report 460 the known variant. The analytics system 100 may further provide 470 a treatment recommendation based on the identified known variant. The analytics system 100 may also report variant metrics calculated based on classified samples. For example, the analytics system 100 may provide aggregated statistics on how many samples are being classified as each variant. These statistics can inform researchers on variant behavior. In embodiments with no identified variant, the analytics system 100 may report the closest match. The analytics system 100 may also notify 480 that there may be a candidate new variant for sequencing. The analytics system 100 may transmit such notifications to a client computing device for a laboratory clinician, a researcher, a healthcare provider, a patient, another healthcare-related professional, or some combination thereof.

Figure 5A:
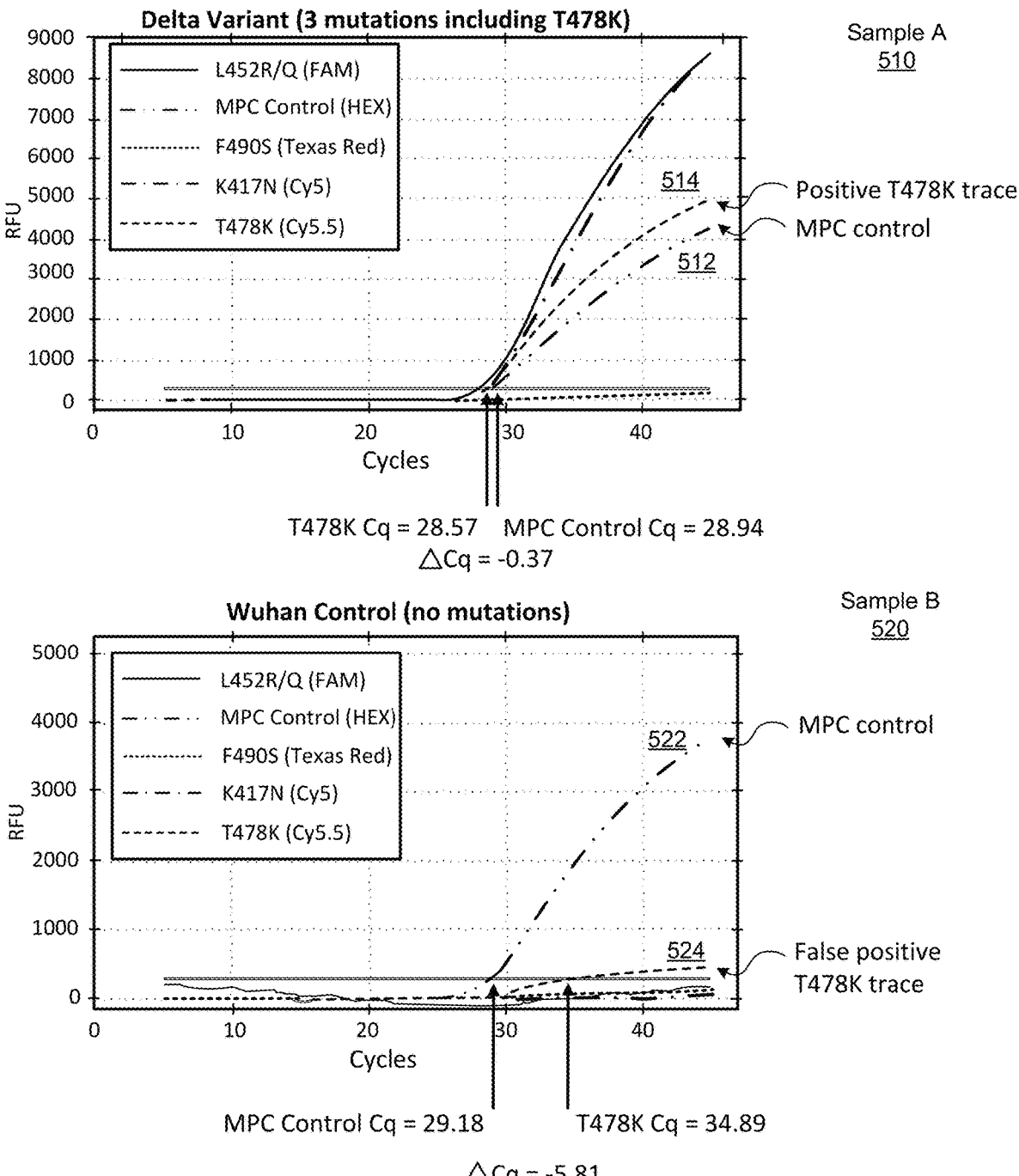
FIG. 5A illustrates example classification of a true positive and a false positive based on delta Cq, according to one or more embodiments.
Figure 5B:
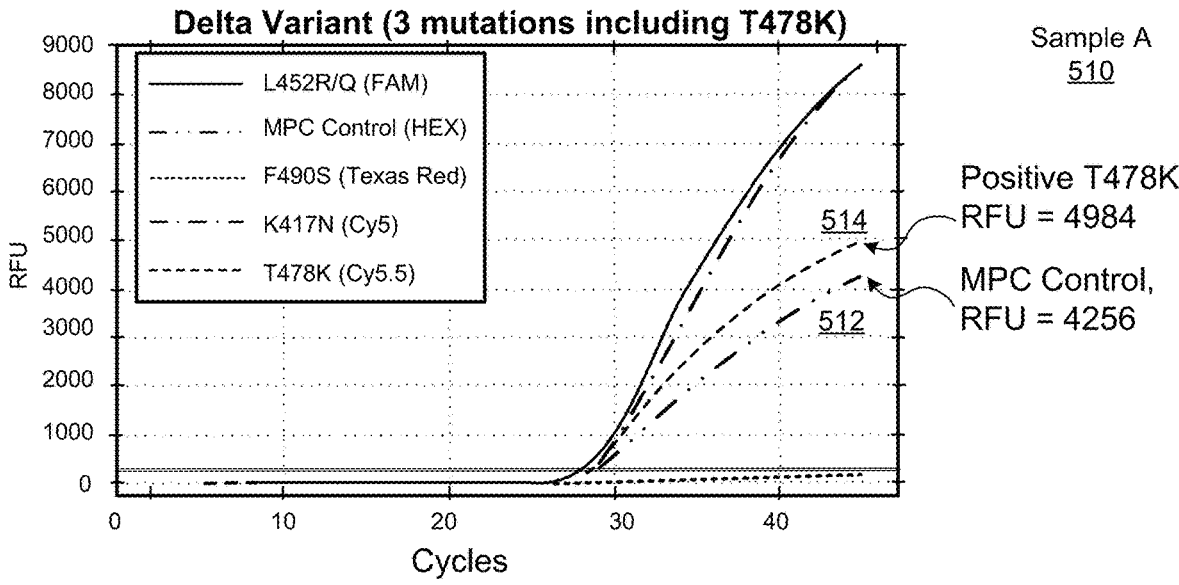
FIG. 5B illustrates example classification of a true positive and a false positive based on peak RFU, according to one or more embodiments.
Figure 5B:
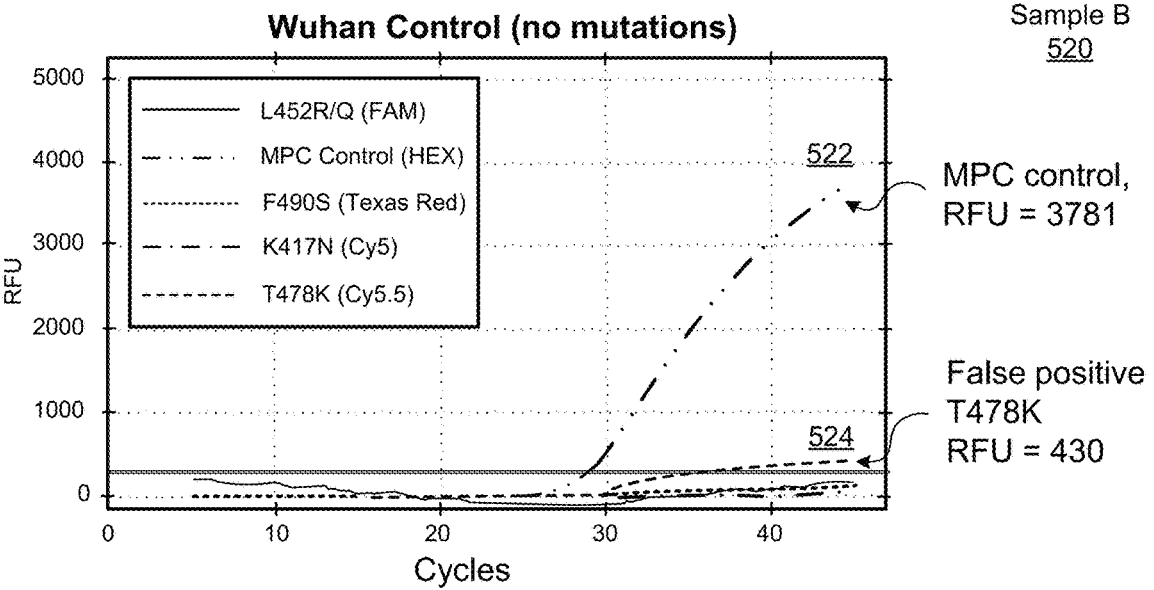

FIGS. 5A & 5B illustrate example mutation detection based on delta Cq and/or RFU ratio, according to one or more embodiments. The analytics system 100 classifies using a multiple mutation assay screening for four mutations: L452R/Q, F490S, K417N, and T478K. Sample A 510 is a sample known to have the Delta variant including three mutations, while Sample B 520 is a sample known as a Wuhan control without mutations. FIGS. 5A & 5B illustrate the analytics system 100 performs the SARS-CoV-2 variant classification 400 of FIG. 4. The analytics system 100 may positively determine mutations by comparing the mutation fluorescence signals to the control fluorescence signal, e.g., determining whether the delta Cq is below a Cq tolerance and/or whether the RFU ratio is above a RFU tolerance.

FIG. 5A illustrates example mutation detection of a true positive and a false positive based on at least delta Cq, according to one or more embodiments. The analytics system 100 measures the Cq for each fluorescence signal that crosses the threshold set ~300 RFU. With Sample A 510, the analytics system 100 measures the Cq for the MPC Control fluorescence signal 512 at 28.94 and the Cq for the T478K fluorescence signal at 28.57. The analytics system 100 calculates the delta Cq by subtracting the MPC Control's Cq from the T478K's Cq, equaling –0.37. Taking a Cq tolerance of 4, the analytics system 100 may detect the T478K mutation based on the delta Cq of –0.37 being below the Cq tolerance of 4. For Sample B 520, the analytics system 100 measures the Cq for the MPC Control fluorescence signal 522 as 29.18 and the Cq for the T478K fluorescence signal as 34.89, with a delta Cq of 5.81. The analytics system 100 determines Sample B 520 as not having the T478K mutation. In such an instance, given that the T478K fluorescence signal 524 did rise above the Threshold RFU at ~300, traditional systems may imprecisely determine the fluorescence signal to sufficiently indicate presence of the T478K mutation.

FIG. 5B illustrates example mutation detection of a true positive and a false positive based on peak RFU, according to one or more embodiments. Sample A 510 and Sample B 520 are the same samples from FIG. 5A with same fluorescence signals. With peak RFU measurements, the analytics system 100, in this embodiment, measures the peak RFU at the last cycle of the qPCR operation. With Sample A 510, the analytics system 100 measures the peak RFU for the MPC Control fluorescence signal 512 to be 4256 and the peak RFU for the T478K fluorescence signal 514 as 4984. The RFU ratio is 4984 to 4256, or 1.17. Taking a RFU tolerance of 0.8, the analytics system 100 may positively detect presence of the T478K mutation. With Sample B 520, the analytics system 100 measures the peak RFU for the MPC Control fluorescence signal 522 as 3781 and the peak RFU for the T478K fluorescence signal 524 as 430. The RFU ratio for the T478K mutation is 0.11. The analytics system 100 determines absence of the T478K mutation as the RFU ratio 0.11 is below the RFU tolerance of 0.8.

In additional embodiments, the analytics system 100 may determine Sample B 520 to be a false positive for the T478K mutation. The T478K fluorescence signal 524 has a trace amount, i.e., surpasses the Threshold RFU of ~300 of baseline noise, but does not have sufficient signal to overcome the delta Cq tolerance and/or the RFU tolerance. As such, the analytics system 100 may determine the T478K mutation to be a false positive, whereas traditional systems may have inaccurately detected the T478K mutation as positive solely based on the crossing of the Threshold RFU.

Exemplary General Computing System

Figure 6:
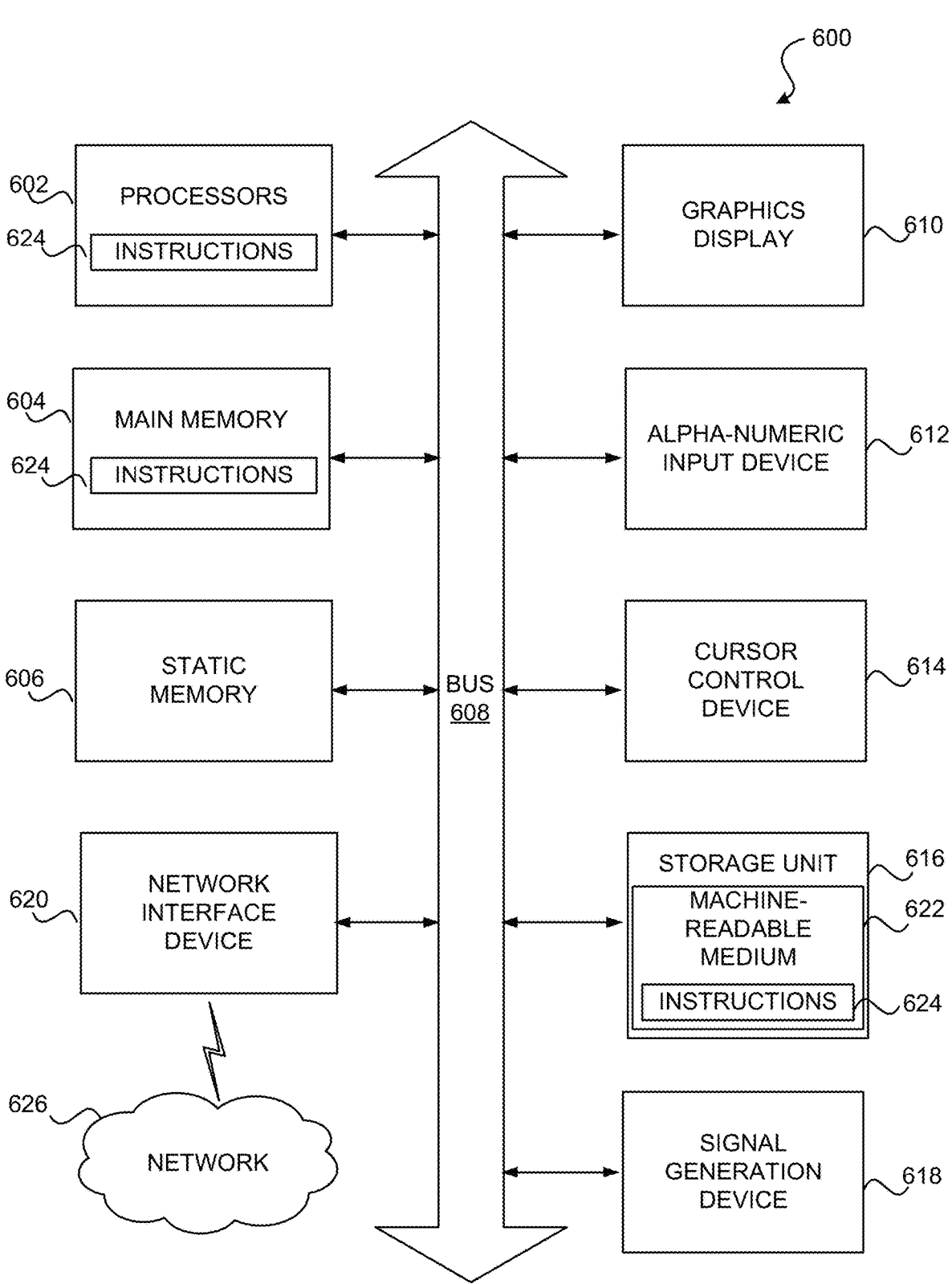
FIG. 6 illustrates a general computing system, according to one or more embodiments.

FIG. 6 illustrates an example general computing system, according to one or more embodiments. Although FIG. 6 depicts a high-level block diagram illustrating physical components of a computer used as part or all of one or more entities described herein, in accordance with an embodiment, a computer may have additional, less, or variations of the components provided in FIG. 6. Although FIG. 6 depicts a computer 600, the figure is intended as functional description of the various features which may be present in computer systems than as a structural schematic of the implementations described herein. In practice, and as recognized by those of ordinary skill in the art, items shown separately could be combined and some items could be separated.

Illustrated in FIG. 6 are at least one processor 602 coupled to a chipset 604. Also coupled to the chipset 604 are a memory 606, a storage device 608, a keyboard 610, a graphics adapter 612, a pointing device 614, and a network adapter 616. A display 618 is coupled to the graphics adapter 612. In one embodiment, the functionality of the chipset 604 is provided by a memory controller hub 620 and an I/O hub 622. In another embodiment, the memory 606 is coupled directly to the processor 602 instead of the chipset 604. In some embodiments, the computer 600 includes one or more communication buses for interconnecting these components. The one or more communication buses optionally include circuitry (sometimes called a chipset) that interconnects and controls communications between system components.

The storage device 608 is any non-transitory computer-readable storage medium, such as a hard drive, compact disk read-only memory (CD-ROM), DVD, or a solid-state memory device or other optical storage, magnetic cassettes, magnetic tape, magnetic disk storage or other magnetic storage devices, magnetic disk storage devices, optical disk storage devices, flash memory devices, or other non-volatile solid state storage devices. Such a storage device 608 can also be referred to as persistent memory. The pointing device 614 may be a mouse, track ball, or other type of pointing device, and is used in combination with the keyboard 610 to input data into the computer 600. The graphics adapter 612 displays images and other information on the display 618. The network adapter 616 couples the computer 600 to a local or wide area network.

The memory 606 holds instructions and data used by the processor 602. The memory 606 can be non-persistent memory, examples of which include high-speed random access memory, such as DRAM, SRAM, DDR RAM, ROM, EEPROM, flash memory.

As is known in the art, a computer 600 can have different or other components than those shown in FIG. 6. In addition, the computer 600 can lack certain illustrated components. In one embodiment, a computer 600 acting as a server may lack a keyboard 610, pointing device 614, graphics adapter 612, or display 618. Moreover, the storage device 608 can be local or remote from the computer 600 (such as embodied within a storage area network (SAN)).

As is known in the art, the computer 600 is adapted to execute computer program modules for providing functionality described herein. As used herein, the term "module" refers to computer program logic utilized to provide the specified functionality. Thus, a module can be implemented in hardware, firmware, or software. In one embodiment, program modules are stored on the storage device 608, loaded into the memory 606, and executed by the processor 602.

Additional Considerations

Some portions of above description describe the embodiments in terms of algorithmic processes or operations. These algorithmic descriptions and representations are commonly used by those skilled in the data processing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments. This is done merely for convenience and to give a general sense of the disclosure. This description should be read to include one or at least one and the singular also includes the plural unless it is obvious that it is meant otherwise.

Upon reading this disclosure, those of skill in the art will appreciate still additional alternative structural and functional designs for a system and a process for verifying an account with an on-line service provider corresponds to a genuine business. Thus, while particular embodiments and applications have been illustrated and described, it is to be understood that the described subject matter is not limited to the precise construction and components disclosed herein and that various modifications, changes and variations which will be apparent to those skilled in the art may be made in the arrangement, operation and details of the method and apparatus disclosed. The scope of protection should be limited only by the following claims.

What is claimed is:

1. A method comprising:

receiving fluorescence signals over a plurality of thermal cycles of a quantitative Polymerase Chain Reaction (qPCR) for a test sample, wherein a first fluorescence signal indicates quantitative presence of a first genomic region as a control for SARS-COV-2, and a second fluorescence signal indicates quantitative presence of a second genomic region of a first mutation present in a subset of variants of SARS-COV-2;

measuring a first quantitative cycle (Cq) for the first fluorescence signal as the first fluorescence signal crosses a threshold relative fluorescence unit (RFU);

measuring a second Cq for the second fluorescence signal as the second fluorescence signal crosses the threshold RFU;

identifying a first peak RFU for the first fluorescence signal;

identifying a second peak RFU for the second fluorescence signal;

calculating a delta Cq as a difference between the second Cq and the first Cq;

calculating a RFU ratio of the second peak RFU to the first peak RFU; and detecting presence of the first mutation based on the delta Cq being below a Cq tolerance or the RFU ratio being above a RFU tolerance.

2. The method of claim 1, wherein a number of thermal cycles is selected between 30 and 100.

3. The method of claim 2, wherein the number of thermal cycles is further selected between 40 and 60.

4. The method of claim 1, wherein the threshold RFU is selected between 5 RFU and 500 RFU.

5. The method of claim 4, wherein the threshold RFU is determined based on the first fluorescence signal.

6. The method of claim 1, wherein the first peak RFU is a maximum RFU of the first fluorescence signal over the plurality of thermal cycles, and wherein the second peak RFU is a maximum RFU of the second fluorescence signal over the plurality of thermal cycles.

7. The method of claim 1, wherein the first peak RFU is a RFU of the first fluorescence signal at a sample thermal cycle of the plurality of thermal cycles, and wherein the second peak RFU is a RFU of the second fluorescence signal at the sample thermal cycle.

8. The method of claim 7, wherein the sample thermal cycle is a final thermal cycle of the plurality of thermal cycles.

9. The method of claim 1, wherein the Cq tolerance is a Cq value selected from the range of 1 Cq to 10 Cq.

10. The method of claim 9, wherein the Cq tolerance is further selected from the range of 2 Cq to 5 Cq.

11. The method of claim 9, wherein the Cq tolerance is selected to minimize false positive detection of the first mutation.

12. The method of claim 1, wherein the RFU tolerance is a ratio selected from the range of 0.3 to 1.1.

13. The method of claim 12, wherein the RFU tolerance is further selected from the range of 0.9 to 1.0.

14. The method of claim 1, wherein detecting the presence of the first mutation is based on the delta Cq being below the Cq tolerance and the RFU ratio being above the RFU tolerance.

15. The method of claim 1, further comprising:

in response to detecting the presence of the first mutation, reporting the test sample as having one of the subset of variants of SARS-COV-2.

16. The method of claim 15, wherein the reporting further comprises reporting a treatment recommendation for treating COVID.

17. The method of claim 1, further comprising:

in response to detecting absence of the first mutation, reporting the test sample as not having any of the subset of variants of SARS-COV-2.

18. The method of claim 17, further comprising:

in response to detecting the absence of the first mutation, identifying the test sample as having a candidate new variant of SARS-COV-2; and providing the test sample for genetic sequencing to sequence the candidate new variant of SARS-COV-2.

19. A non-transitory computer-readable storage medium storing instructions that, when executed by a computer processor, cause the computer processor to perform operations comprising:

receiving fluorescence signals over a plurality of thermal cycles of a quantitative Polymerase Chain Reaction (qPCR) for a test sample, wherein a first fluorescence signal indicates quantitative presence of a first genomic region as a control for SARS-COV-2, and a second fluorescence signal indicates quantitative presence of a second genomic region of a first mutation present in a subset of variants of SARS-COV-2;

measuring a first quantitative cycle (Cq) for the first fluorescence signal as the first fluorescence signal crosses a threshold relative fluorescence unit (RFU);

measuring a second Cq for the second fluorescence signal as the second fluorescence signal crosses the threshold RFU;

identifying a first peak RFU for the first fluorescence signal;

identifying a second peak RFU for the second fluorescence signal;

calculating a delta Cq as a difference between the second Cq and the first Cq;

calculating a RFU ratio of the second peak RFU to the first peak RFU; and detecting presence of the first mutation based on the delta Cq being below a Cq tolerance or the RFU ratio being above a RFU tolerance.

20. A system comprising:

a computer processor; and a non-transitory computer-readable storage medium storing instructions that, when executed by the computer processor, cause the computer processor to perform operations:

receiving fluorescence signals over a plurality of thermal cycles of a quantitative Polymerase Chain Reaction (qPCR) for a test sample, wherein a first fluorescence signal indicates quantitative presence of a first genomic region as a control for SARS-COV-2, and a second fluorescence signal indicates quantitative presence of a second genomic region of a first mutation present in a subset of variants of SARS-COV-2;

measuring a first quantitative cycle (Cq) for the first fluorescence signal as the first fluorescence signal crosses a threshold relative fluorescence unit (RFU);

measuring a second Cq for the second fluorescence signal as the second fluorescence signal crosses the threshold RFU;

identifying a first peak RFU for the first fluorescence signal;

identifying a second peak RFU for the second fluorescence signal;

calculating a delta Cq as a difference between the second Cq and the first Cq;

calculating a RFU ratio of the second peak RFU to the first peak RFU; and detecting presence of the first mutation based on the delta Cq being below a Cq tolerance or the RFU ratio being above a RFU tolerance.

* * * * *